United States Patent [19]

Jamas et al.

[11] Patent Number: 4,810,646
[45] Date of Patent: Mar. 7, 1989

[54] GLUCAN COMPOSITIONS AND PROCESS FOR PREPARATION THEREOF

[75] Inventors: Spiros Jamas; ChoKyun Rha; Anthony J. Sinskey, all of Boston, Mass.

[73] Assignee: Massachusetts Institute of Technology, Cambridge, Mass.

[21] Appl. No.: 675,927

[22] Filed: Nov. 28, 1984

[51] Int. Cl.$^4$ .................... C12P 19/04; C08B 37/00; C12N 1/18

[52] U.S. Cl. .................... 435/101; 536/123; 435/256

[58] Field of Search .................... 435/101, 255, 256; 514/54; 536/1.1, 123

[56] References Cited

PUBLICATIONS

Manners et al, "The Structure of a $\beta$-(1-3)-D-Glucan from Yeast Cell Walls", *Biochem J.*, 135:19-36, (1973).

Sietsma, et al., *Journal of General Microbiology*, 114:99-108 (1979); 125:209-212 (1981).

Kreger, et al., *Journal of General Microbiology*, 92:207-220 (1975).

Kopecka, et al., *The Journal of Cell Biology*, 62, 66-76 (1974).

*Primary Examiner*—John Tarcza
*Attorney, Agent, or Firm*—Hamilton, Brook, Smith & Reynolds

[57] ABSTRACT

Three dimensional glucan matrix compositions are prepared by separating growing *Saccharomyces cerevisiae* yeast from its growth medium, subjecting the yeast with cell walls intact to aqueous hydroxide and treating the insoluble glucan with acetic acid to alter the $\beta(1-6)$ linkages. The glucans have viscosity characteristics dependent upon the strain of *Saccharomyces cerevisiae* utilized and are useful as stabilizer or thickeners.

13 Claims, 3 Drawing Sheets

VISCOSITY PROFILE OF A364A GLUCAN SHOWING THE EFFECT OF 4h LAMINARINASE DIGEST

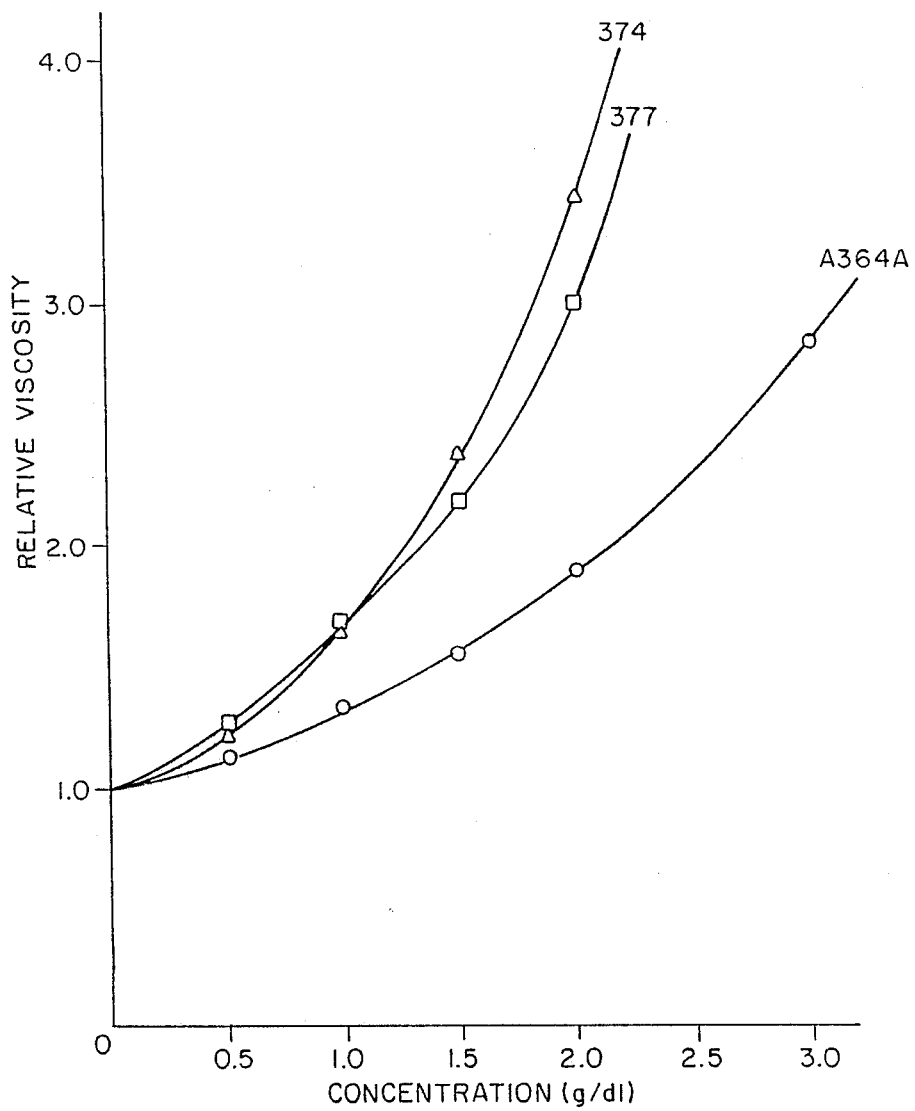
FIG. 1. VISCOSITY PROFILES OF YEAST GLUCAN COMPARING DIFFERENT CELL MORPHOLOGIES

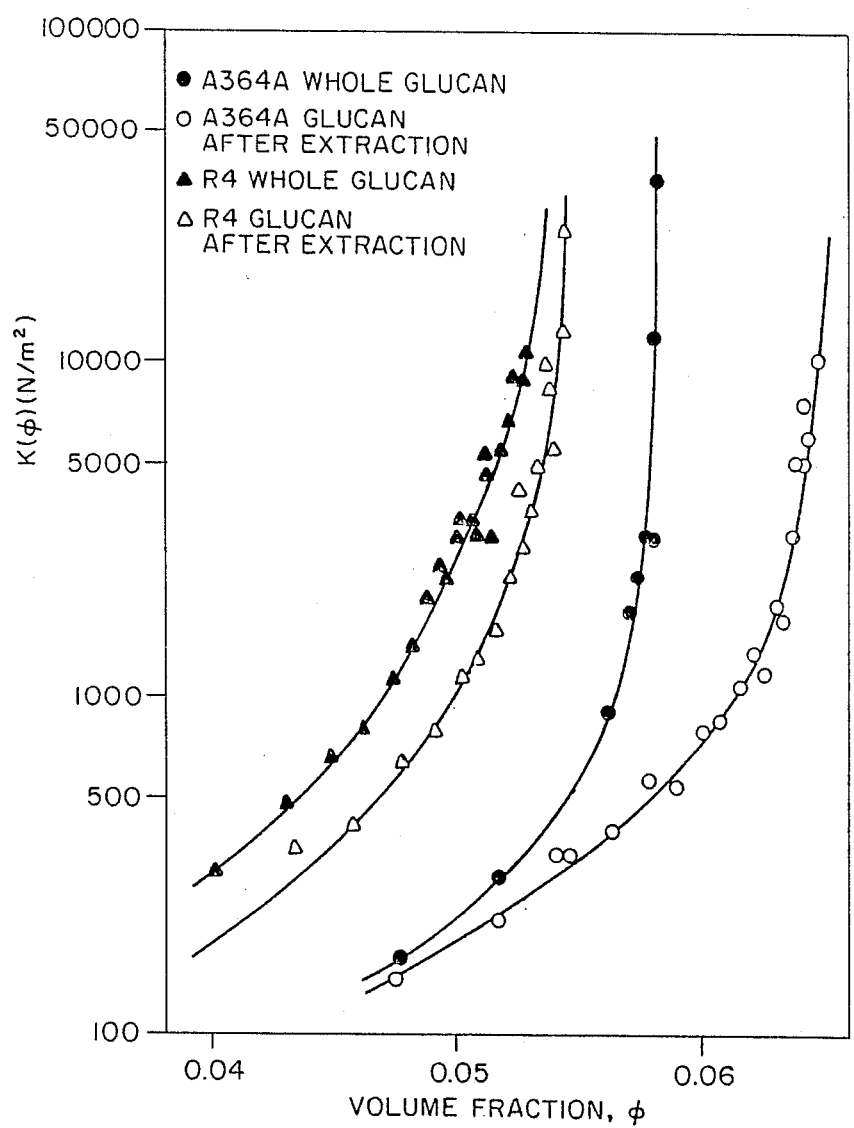
FIG. 2. PLOT OF THE NETWORK-COMPRESSION MODULUS VS. VOLUME FRACTION GLUCAN SUSPENSIONS (TIME = 60 MINUTES)

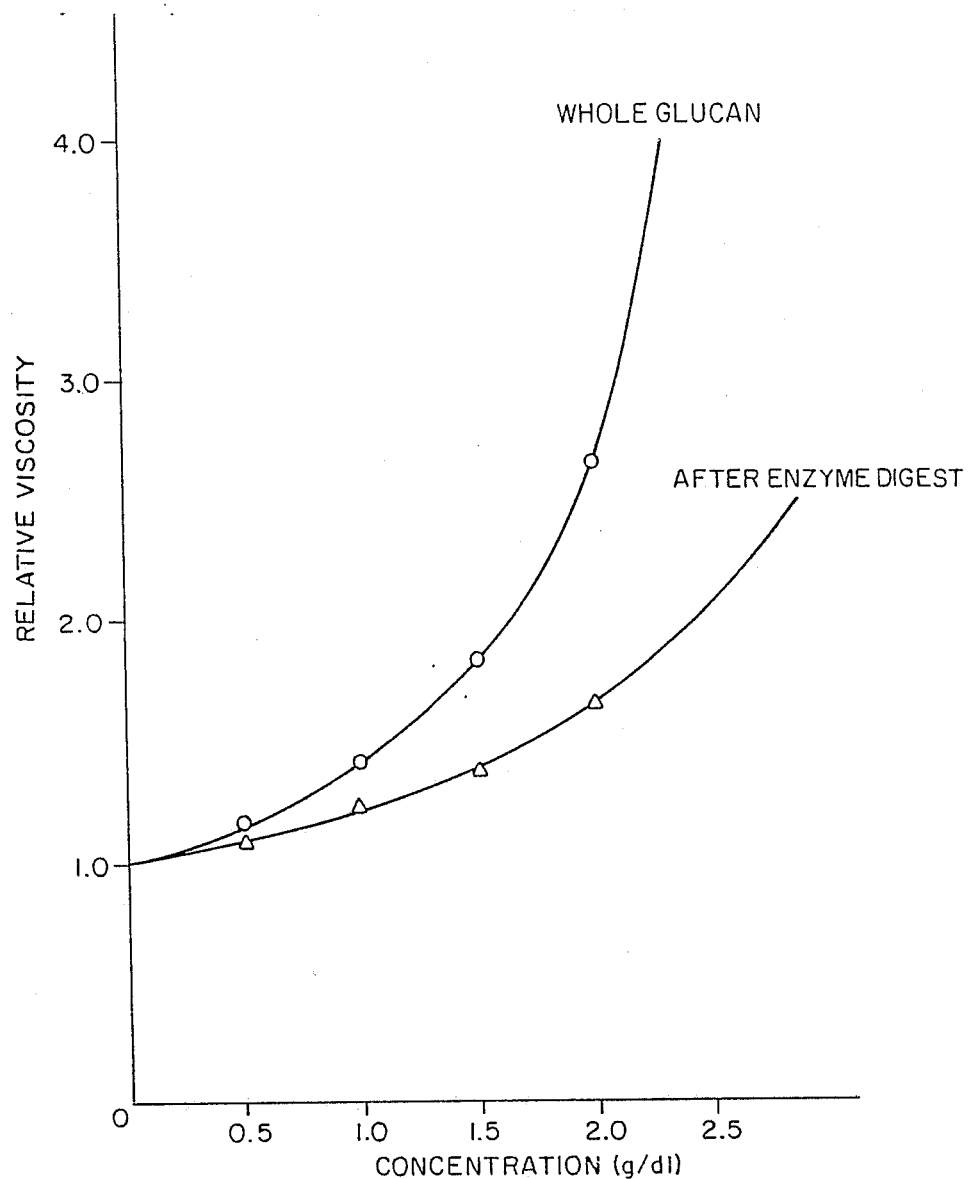
FIG. 3. VISCOSITY PROFILE OF A364A GLUCAN SHOWING THE EFFECT OF 4h LAMINARINASE DIGEST

GLUCAN COMPOSITIONS AND PROCESS FOR PREPARATION THEREOF

FIELD OF THE INVENTION

The present invention relates to three dimensional glucan matrices derived from strains of Saccharomyces cerevisial and processes for their preparation.

BACKGROUND OF THE INVENTION

The food industry uses many naturally derived polysaccharides as stabilizers and thickeners. Other industries use polysaccharides as water treatment chemicals, viscosifiers, thickeners and as surface active materials. Products such as carrageenan, alginate and starch, exhibit unique structural and theological properties such as yield stress and an ability to increase the viscosity in an aqueous environment. The specific structure-function relationships of these biopolymers depend on the individual components such as monomers or repeating units and their chemical linkages.

Polysaccharides which form the bulk of biopolymers in the microbial world have already been noted for their structural importance and are responsible for maintaining the integrity of bacteria and fungi. With the advent of genetic engineering, biosynthesis and manufacture of these biopolymers can be directed to produce molecules with altered physical properties.

Yeast has historically earned its role as an important food grade and industrial organism. The cell wall of Saccharomyces cerevisiae is mainly composed of β-linked glucan. This polymer is responsible for the shape and mechanical strength of the cell walls. The glucan is mainly composed of a backbone chain of $\beta(1-3)$ linked glucose units with a low degree of inter and intramolecular branching through $\beta(1-6)$ linkages. A minor component that consists mainly of a highly branched $\beta(106)$ linked glucan is closely associated with the main component and both comprise the alkali insoluble glucan fraction.

The following articles deal with the structure of glucans: The Structure of a $\beta$-(1-6)-D-Glucan from Yeast Cell Walls by Manners et al., Biochem. J. (1973) 135, 31–36; Evidence for Covalent Linkages between Chitin and β-Glucan in Fungal Wall by Seitsma et al., Journal of General Microbiology (1979), 114, 99–108; Demonstration of a Fibrillar Component in the Cell Wall of the Yeast Saccharomyces cervisiae and its Chemical Nature, by Kopecka et al., The Journal of Cell Biology, Vol. 62 (1974), 66–76; On the Nature and Formation of the Fibrillar Nets Produced by Photoplasts Saccharomyces Cerevisiae in Liquid Media: An electromicroscopic, X-Ray Diffraction and Chemical Study by Kreger et al., Journal of General Microbiology (1975), 92, 202–220; Short Communication Solubility of (13)-β-D-(1-6)-β-D-glucan in Fungal Walls: Important of Presumed Linkage between Glucan and Chitin.

In the prior art processes, aqueous hydroxide extraction of the Yeast Saccharomyces cerevisiae has been practiced, but with a prior step of disrupting the cell walls. This procedure required that the extraction steps be conducted under relatively mild conditions to avoid product degradation. This, in turn, led to the need for multiple extraction steps over a long time period, and therefore is undesirable.

SUMMARY OF THE INVENTION

By processing Saccharomyces cerevisiae strains and the glucans therefrom according to the techniques of the present invention, a product which retains a rigid three dimensional morphology and having high water holding capacity is formed which in turn may be further processed to give glucans having additional favorable properties.

In accordance with the present invention, there is provided an aqueous hydroxide insoluble glucan derived from a yeast strain and having less than one percent by weight protein, said glucan being a Saccharomyces cerevisiae A364A derived glucan having a particle size of from about 2 to about 4 microns with a viscosity of about 1000 centipoise in an aqueous suspension containing about 5.5 grams of glucan per deciliter, or a Saccharomyces cerevisiae 374 derived glucan having a particle size of from about 2.5 to about 6.3 microns with a viscosity of about 2630 centipoise in an aqueous suspension containing about 3.5 grams of glucan per deciliter, or a Saccharomyces cerevisiae R4 derived glucan having a particle size of from about 2 to about 4 microns with a viscosity of about 1000 centipoise in an aqueous suspension containing about 5.5 grams of glucan per deciliter.

Also provided is an aqueous hydroxide insoluble glucan derived from a strain of Saccharomyces cerevisiae, said glucan having altered $\beta(1-3)$ linkages for depressing the aqueous viscosity.

Further, in accordance with the present invention, there is provided an aqueous hydroxide insoluble glucan derived from a mutant strain of Saccharomyces cerevisiae, said glucan having altered $\beta(1-6)$ linkages for enhancing the aqueous viscosity.

The glucans as set forth above are produced by processes described hereinafter.

DETAILED DESCRIPTION OF THE INVENTION

The glucan production process described below can be separated into two steps. The first step involves the extraction and purification of the alkali-insoluble glucan fraction from Saccharomyces cerevisiae cell walls. This process yields a product which maintains the structural properties of the glucan as found in vivo and will be referred to as whole glucan. Thus, the structure-function properties of the whole glucan preparation depend directly on the source (strain) from which it is obtained. The second step involves the modification of the whole glucan structure using chemical or enzymatic treatment. In this step the structure-function properties of the whole glucan can be altered in a controllable manner. In other words, the viscosity of aqueous suspensions of glucan can be adjusted by specific chemical or enzymatic modifications.

The yeast strain employed are Saccharomyces cerevisiae and mutants therefrom. Saccharomyces cerevisiae A364A and its two temperature sensitive, cell division cycle mutants, Saccharomyces cerevisiae 374 and 377 are preferred strains.

Strains A364A, 374 and 377 are available to the public through L.A. Hartwell, Department of Genetics, University of Washington, Seattle and from the Yeast Genetics Stock Center, Berkeley, California. Furthermore, the strain Saccharomyces cerevisiae R4 is a mutant of A364A which we have insolated on the basis of an increased $\beta(1-6)$ glucan fraction and is also employed to obtain glucan matrices with altered structure-function properties.

The following procedure is employed to isolate mutant R4.

Strain A364A is grown in 100 ml YPD to mid-log phase. The cells are washed in 0.1 M MgSO$_4$ and divided into 5 ml aliquots in sterile glass petri plates. A UV exposure of 25 sec (30% survival) is used. The cells are then suspended in 5 ml YPD and grown under subdued light to a concentration of $5 \times 10^6$ CFU/ml. The cells are harvested, and protoplasts are as described using 0.25 mg/ml laminarinase for 30 minutes. The suspension is then diluted with water to lyse osmotically sensitive protoplasts. The surviving cells then are grown in 5 ml YPD to a density of approximately $5 \times 10^6$ CFU/ml (approximately 10 hours). The laminarinase treatment followed by growth is repeated two more times using 1.0 mg/ml enzyme for 15 minutes. The candidates which showed resistance to laminarinase digestion are then streaked on YPDA plates. Single colony isolates are tested for resistance to the enzyme compared to the resistance of the control strain, A364A. The mutant R4 is available from the Agricultural Research Service under No. NRRL Y-15903.

The yeast cells may be produced by methods known in the art. Typical growth mediums comprise glucose, peptone and a yeast extract. Prior to removing the yeast cells from the growth medium it is desirable to stop the cell division temperature by altering the growth. With the yeast cells utilized in the present invention, this may be conveniently performed by a sudden reduction in temperature. This reduction in temperature ensures that no glycogen will be formed which would interfere with the extraction of the glucans. This step is a precautionary measure to avoid the need for extra glycogen extractions. A pure glucan is thus obtained.

The grown culture of yeast cells may be harvested and separated from the growth medium by methods typically applied to separate the solid cell structure from the liquid medium. Such methods typically employ a solid-liquid separation process such as filtration or centrifuging.

The herein referred to first step according to the process of the present invention, is treating the yeast with an aqueous hydroxide solution at a suitable concentration to solubilize a portion of the yeast and form an aqueous hydroxide insoluble glucan having $\beta(1-6)$ and $\beta(1-3)$ linkages. Preferably, the starting yeast consist essentially of purified yeast absent impurities from the growth medium. Starting with yeast compositions that are less concentrated, consumption of the aqueous hydroxide reactants and controlling the concentration of reactants in the preferred ranges is more difficult.

The treating step is performed by digesting the yeast in the aqueous hydroxide solution. The protein portion of the cell is solubilized in the aqueous portion to leave a glucan devoid of protein and having a substantially unaltered structure of $\beta(1-6)$ and $\beta(1-3)$ linkages. The preferred proper conditions of performing this step results in the mannan layer of the cell wall being dissolved to the aqueous hydroxide solution. The intercellular constituents are digested and reacted to form smaller molecules of protein which are transported through the cell wall. Preferably, the conditions of digestion are such that at least in a major portion of the cells, the cell walls are not destroyed. More preferably, substantially all the cellular wall material remains unaltered.

The aqueous hydroxide digestion step is preferably carried out in a hydroxide solution having an initial pH of from about 4.0 to 12.5 or a normality of from about 0.75 to about 1.5. Typical hydroxide solutions include hydroxides of the alkali metal group and alkaline earth metals of the Periodic Table. The preferred aqueous hydroxide solutions are of sodium and potassium due to its availability. The digestion is preferably carried out at a temperature of from about 25° C. to about 100° C. with lower temperatures requiring longer digestion times. When sodium hydroxide is used as the aqueous hydroxide, the temperature is preferably from about 80° C. to about 100° C. and the solution has an initial normality of from about 0.75 to about 1.5. The hydroxide added is in excess of the amount required, thus, no additions are necessary.

From about 50 to about 100 parts by weight hydroxide solution per part of yeast is used. Preferably the aqueous hydroxide digestion step is carried out by a series of contacting steps so that the amount of hydroxide solution needed is less than if only one contacting step is utilized. In other words, it is desirable to remove a portion of protein material from the cell. Preferably such removal is carried out to such an extent that less than one percent of the protein remains with the cell or glucan, even more preferably, less than one percent remains with the cell. The digested yeast is preferably subjected to further washings and extractions to reduce the protein level to the preferred amount hereinbefore indicated.

By conducting this process without a step of disrupting the cell walls, the extraction can be conducted at more severe conditions of pH and temperature than was possible with the prior art procedure which included a step of disrupting the cell walls. That is, the process of this invention avoids product degradation while employing these severe extraction conditions which permits elimination of time consuming multiple extraction steps.

After the above aqueous hydroxide treatment step, the final whole glucan product comprises about 10 to about 15 percent of the initial weight of the yeast cell, preferably the product is from about 12 to about 14, and more preferably about 14 percent by weight.

The aqueous hydroxide insoluble glucan produced is as set forth in the summary of the invention.

The second step as set forth above, involves the modification of a whole glucan as produced above by chemical treatment to change the properties of the glucan. According to a first chemical treatment the whole glucan is treated with acetic acid to increase the viscosity. According to a second chemical treatment the whole glucan is treated with an enzyme to decrease the viscosity. It is contemplated that whole glucans, in addition to those particular mutants described above, may be used, provided that the glucans are derived from a strain of *Saccharomyces cerevisiae* or even from a very broad spectrum of yeast strains. The processing conditions described above are applicable to glucan extraction from fungi in general. The properties of these glucans also will depend on the sources from which they are derived.

In accordance with the principles of the present invention, there is provided a process for preparing an altered aqueous hydroxide insoluble glucan by treating the insoluble glucan with acetic acid at a suitable concentration and at a suitable temperature for a suitable period of time to alter the $\beta(1-6)$ linkages. The acetic acid treatment specifically affects the β(1-6) fraction (approximately 4 percent of whole glucan). Acetic acid is the only acid that is effective in this extraction. Preferably, the treatment is carried out to such an extent to remove from about 3 to about 5 percent by weight of the glucan based on total weight of the glucan before treatment, more preferably the extent of removal is from about 3 to about 4 percent by weight. The preferred compositions formed demonstrate an enhancement in viscosity after treatment.

The acetic acid treatment is carried out under conditions to substantially only affect the β(1-6) linkages and portions of structure that contribute to a decreased viscosity. Preferably, the acetic acid treatment is carried out with a liquid consisting essentially of acetic acid. Any dilution in the acetic acid with additional ingredients should only be in the extent not to effect the above desired results. Impurities will not affect the action of acetic acid or the glucan. Typical dilutions might be organic solvents or inorganic acid solutions. The treatment is preferably carried out at a temperature of from about 55° C. to about 85° C. The extraction time for this step is only critical within the first 3 hours. After this, exceedingly smaller amounts of the β(1-6) fraction are removed making the process less economical.

The second chemical treatment is with an enzyme laminarinase for altering the β(1-3) linkages to decrease the viscosity of the glucan in aqueous solutions, a hydrodynamic parameter ($k_1$) of the final treated product having altered linkages is dependent on the treatment time according to the final formula:

$$K_1 = -0.0021 \text{ (time)} + 0.26$$

where time is in minutes
where time is less than o ne hour

The parameter $K_1$ is directly related (proportional) to the relative viscosity. In the case of aqueous suspensions the relative viscosity is equal to the actual viscosity when the latter is measured in centipoise.

The enzyme treatment is carried out in an aqueous solution having a concentration of glucan of from about 0.1 to about 2.0 grams per liter and a concentration of enzyme of from about 0.10 to about 1.0 gram per liter. At the above concentrations, the time of incubation may vary from 10 minutes to about 4 hours. The incubation may be halted by a temperature shift. By operating in this manner, it is possible to control product viscosity precisely for particular usage, as, for example, with a variety of food products. In the viscosity measurements the contribution of enzyme is removed but in any case is negligible. The enzyme can be removed easily by current practices of protein separation such as salting out.

A process for preparing an aqueous slurry of a glucan having a predetermined desired viscosity is provided. The slurry comprises glucan at a concentration which is a function of the predetermined desired viscosity according to the following approximate formula:

$$1/\text{concentration} = K_1(1/\log(\text{relative viscosity})\text{-}) + K_2$$

where, $K_1$ = (shape factor) x (hydrodynamic volume)
$K_2$ = (hydrodynamic volume)/(maximum packing fraction) The shape factor is an empirically determined value which describes the shape of the glucan matrix in its aqueous environment. The shape factor is a function of the length:width ratio of a particle and can be determined microscopically. The hydrodynamic volume is a measure of the volume a particle occupies when in suspension. This is an important parameter for glucan suspension as it indicates the high water holding capacity of glucan matrixes. The maximum packing fraction can be described as the highest attainable volume fraction of glucans which can be packed into a unit volume of suspension.

EXAMPLE 1

In this example, glucan is prepared from *Saccharomyces cerevisiae* A364A, 374, 377 and R4. The respective yeast strains stored on slants at 4° C. were inoculated into tubes containing 5 milliliter of autoclaved liquid growth medium at pH 5.5 The growth medium comprised 2 percent glucose, 2 percent peptone and 1 percent yeast extract in percent milligrams per deciliter. The tubes were incubated on a shaker at 30° C. until the cells reached stationary growth phase as determined by measuring turbidity in a Klett-Summerson colorimeter. The 5 milliliter stationary cultures were then inoculated into baffled, Erlenmeyer flasks containing 250 milliliters autoclaved growth medium at pH 5.5. The flasks were incubated on a shaker at 30° C. to the stationary growth phase. These cultures were used as inoculum for batch fermentation. A Chemap fermenter was used to produce the biomass. A volume of 10 liters of growth medium was added to the fermenter and the pH was brought to 5.5. About 0.5 milliliters of polyethyleneglycol (P-2000) was added as antifoam. The medium was sterilized in the fermenter itself by heating to 120° C. and holding at this temperature for 30 minutes. The medium was allowed to cool and the temperature control was set at 28° C. The pH of the medium was maintained at 5.5 +0.1. The impeller speed was set to 400 rpm and an aeration rate of 1 vvm was used. After 1 hour was allowed for the operating condition to reach steady-state, the 250 milliliter inoculum was added to the fermenter. The growth of the cells was followed by removing 10 milliliter samples and measuring the turbidity in a Klett-Summerson colorimeter. In the fermentation of strains 374 and 377 and a temperature shift to 37° C. was performed at the early exponential growth phase. This was equivalent to a Klett reading of approximately 30 units. The temperature shift was made by disconnecting the temperature control, then heating the culture to 37° C. by passing steam through the heat transfer coils. The temperature control was then set to 37° C. The growth characteristics of the strains are summarized in Table 2:

TABLE 2

| | Yeast Fermentation | | |
|---|---|---|---|
| Strain | Temperature (°C.) | Specific Growth Rate (h$^{-1}$) | Doubling Time (min) |
| A354A | 28 | 0.45 | 92 |
| 374 | 28 | 0.16 | 246 |
| 374 | 37 | 0.27 | 154 } ~1.5 × 4 |
| 377 | 28 | 0.25 | 162 |
| 377 | 37 | 0.32 | 129 |

The fermentation was stopped at the late exponential growth phase which corresponds to approximately 120 Klett units.

The cells were harvested by batch centrifugation at 8000 rpm for 20 minutes in a Sorval RC2-B centrifuge. The cells were then washed twice in citrate-phosphate buffer at pH 5.5 in order to prepare them for the extraction of the whole glucan. The first step involves resuspending the cell mass in 1 liter, 4% w/v NaOH and heating to 100° C. The cell suspension is stirred vigorously for 1 hour at this temperature. The suspension is allowed to cool to room temperature and 1 liter cold, distilled water is added to stop the reaction. The insoluble material containing the cell walls is recovered by centrifuging at 2000 rpm for 15 minutes. This material is then suspended in 2 liters, 3% w/v NaOH and heated to 75° C. The suspension is stirred vigorously for 3 hours at this temperature. The suspension is then allowed to cool to room temperature and the extraction is continued for a further 16 hours. 1 liter of cold distilled water is then added. The insoluble residue is recovered by centrifugation at 2000 rpm for 15 minutes. This material is finally extracted in 2 liters, 3% w/v NaOH brought to pH 4.5 with HCl, at 75° C. for 1 hour. The insoluble residue is recovered by centrifugation and washed three times with 200 milliliters water, once with 200 milliliters dehydrated ethanol and twice with 200 milliliters dehydrated ethyl ether. The resulting slurry is placed on petri plates and air dried at 37° C. for 12 hours to a fine white powder. An example of the yields obtained from this extraction and purification process is shown in Table 3:

TABLE 3

| Glucan Extraction from *Saccharomyces cerevisiae* A3654A | | | |
|---|---|---|---|
| Dry cell weight (g) | 14.03 | 15.25 | 9.78 |
| Glucan fraction (g) | 1.86 | 1.64 | 1.53 |
| % DCW extracted | 13 | 11 | 15 |
| Amino acid content Lysine equivalent (% w/w) | 0.73 | 0.81 | 0.88 |

Although a small quantity of protein was detected in the glucan preparations, we proved that the overwhelming component in this preparation is β-glucan. The purity of this preparation was tested by obtaining infra-red spectra of the whole glucan samples. Samples were prepared in solid kBr discs and analyzed in a Perkin-Elmer infra-red Spectrophotometer. The spectra obtained were compared with the spectrum of a standard β-glucan, Laminarin purchased from Sigma Chemical Company. The whole glucan samples from all three strains gave characteristic spectra of glucan. All the peaks characteristic of the β-glucan structural backbone at 7.95, 8.35, 8.7 and 11.3 μm were obtained for both the whole glucan samples.

The whole glucan powder was then rehydrated in distilled water in order to determine the viscosity profile of the suspension. Viscosity was measured using a Cannon-Fenske routine viscometer (size 75). The viscosity profiles of glucan suspensions for the three strains are shown in FIG. 1.

The units of concentration in g/dl (g/100 milliliters) are equivalent to % w/v. By applying the linear model which was discussed in the detailed description of this disclosure, the relevant information concerning the hydrodynamic properties of the glucan preparation was obtained. The accuracy of this model is reflected in the values of the regression coefficient, r, shown in Table 4:

TABLE 4

| Hydrodynamic Properties of Whole Yeast Glucan | | | | |
|---|---|---|---|---|
| Glucan Sample | Regression Coefficient r | Shape Factor v | Hydrodynamic Volume v (dl/g) | $\phi_m$ |
| A364A | 0.9986 | 2.5 | 0.092 | 0.63 |
| 374 | 0.9987 | 4.1 | 0.088 | 0.36 |
| 377 | 0.9974 | 4.1 | 0.091 | 0.45 |
| R4 | 0.9995 | 2.5 | 0.087 | .66 |

1. $\phi_m$ = Maximum packing fraction

Table 4 shows the concentration of glucan required to produce a viscosity of 100 cp, 50,000 cp and 100,000 cp at 25° C.

The whole glucan produced from mutant R4 has an identical viscosity profile to that of whole glucan from A364A, however, by increasing the degree of β(1–6) crosslinking in vivo a glucan matrix has been developed with a significantly higher mechanical strength. The strength (rigidity) of the glucan matrices was measured using centrifugal compression of the glucan matrices.

TABLE 5

| The Concentration of Various Whole Glucan Suspensions Required to Produce a Range of Viscosities at 25° C. | | | |
|---|---|---|---|
| | Concentration in % w/v (g/dl) | | |
| Source of Glucan | 1000 cp | 50,000 cp | 100,000 cp |
| A364A | 5.5 | 5.8 | 5.9 |
| 374 | 3.4 | 3.7 | 3.7 |
| 377 | 3.9 | 4.3 | 4.3 |
| R4 | 5.8 | 6.2 | 6.3 |

Table 6 illustrates the structural rigidity (electric modulus) of whole glucan matrices.

TABLE 6

| The Elastic Modulus of Whole Glucan Matrices Measured in the Range 0–30 g | | | | |
|---|---|---|---|---|
| | Network Modulus (Nm$^{-2}$) | | | |
| Source | $\phi = 0.048$ | 0.050 | 0.052 | 0.054 |
| A364A Whole Glucan | 170 | 225 | 310 | 480 |
| R4 Whole Glucan | 1300 | 2400 | 6000 | 42000 |

EXAMPLE 2

This example concerns the acetic acid treatment of *Saccharomyces cerevisiae* A364A whole glucan in acetic acid. A 500 mg sample of whole glucan from *S. cerevisiae* A364A is suspended in 250 milliliters of 0.5 M acetic acid. The suspension is continuously stirred at 90° C. for 3 hours. At the end of this extraction, the remaining insoluble glucan residue is recovered by batch centrifugation at 5000 rpm for 20 minutes. The glucan residue is washed once in 200 milliliters distilled water, once in 200 milliliters dehydrated ethanol and twice in 200 milliliters dehydrated ethyl ether. The resulting slurry is dried in air at 37° C. for 12 hours. The initial suspension in acetic acid and the supernatant were arrayed for total carbohydrate to determine the proportion of the extractable β(1–6) glucan component. The white glucan powder obtained after drying is resuspended in distilled water to determine its viscosity profile. As shown in FIG. 2, chemical modification of A364A glucan by acetic acid has an insignificant effect on the viscosity characteristics. However, measurement of the elastic modulus of the glucan matrices shows that their structural rigidity can be controlled by the extent of the acetic acid extraction. FIG. 3 illustrates the effect of the acetic extraction on the structural rigidity of R4 whole glucan and compares this to glucan extracted from strain A364A.

EXAMPLE 3

A 500 milligram sample of whole glucan from Saccharomyces cerevisiae 374 is suspended in 250 milliliters, 0.5 M acetic acid. An identical procedure to that outlined in Example 2 is followed. In this case, extraction in hot acetic acid causes an increase in the thickening properties of the glucan as shown in FIG. 2.

TABLE 7

The Viscosity of a Suspension of 374 Whole Glucan Compared to 374 Glucan After Acetic Acid Extraction for a Range of Concentrations

| Source of Glucan | Viscosity in Centipoise, 25° C. | | | | |
|---|---|---|---|---|---|
| | 2% | 2.5% | 3% | 3.5% | 3.7% |
| 374 (Whole Glucan) | 1.5 | 2.8 | 7.1 | 14.2 | 20.1 |
| 374 (After Extraction) | 1.6 | 4.7 | 58.3 | 1879.0 | 33844.5 |

EXAMPLE 4

A 500 milligram sample of 377 whole glucan is suspended in 150 milliliters, 0.5 M acetic acid. An identical procedure to that outlined in Example 2 is followed.

The effect of this process on the viscosity profile of 377 glucan is similar to that illustrated in FIG. 2.

TABLE 8

The Viscosity of a Suspension of 377 Whole Glucan Compared to 377 Glucan After Acetic Acid Extraction for a Range of Concentration

| Source of Glucan | Viscosity in Centipoise, 25° C. | | | | |
|---|---|---|---|---|---|
| | 2% | 2.5% | 3% | 3.5% | 3.7% |
| 377 (Whole Glucan) | 1.6 | 3.4 | 16.0 | 75.0 | 193.5 |
| 377 (After Extraction) | 1.7 | 4.7 | 58.3 | 1878.0 | 33844.5 |

The effect of the acetic acid treatment on the hydrodynamic properties of the glucan as determined by the linear model is summarized in Table 10.

EXAMPLE 5

A 500 milligram sample of whole glucan from Saccharomyces cerevisiae R4 is suspended in 250 milliliters, 0.5 M acetic acid. An identical procedure to that outlined in Example 2 is followed.

In this case the whole glucan sample has an identical viscosity profile to the whole glucan from strain A364A, however, after the extraction the thickening properties are enhanced considerably.

TABLE 9

The Viscosity of a Suspension of R4 Whole Glucan Compared to R4 Glucan After Acetic Acid Extraction for a Range of Concentrations

| Source of Glucan | Viscosity in Centipoise, 25° C. | | | | |
|---|---|---|---|---|---|
| | 2% | 2.5% | 3% | 3.5% | 3.7% |
| R4 (Whole Glucan) | 1.8 | 2.3 | 3.1 | 4.5 | 5.4 |
| R4 (After Extraction) | 2.6 | 4.6 | 12.4 | 106.3 | 636.7 |

TABLE 10

Hydrodynamic Properties of Glucan After Acetic Acid Extraction

| Sample | Regression Coefficient r | Shape Factor V | Hydrodynamic Volume v (dl/g) | $\phi_m$ |
|---|---|---|---|---|
| A364A Whole Glucan | 0.9999 | 2.5 | 0.106 | 0.46 |
| A364A After Extn. | 0.9974 | 2.5 | 0.103 | 0.47 |
| 374 Whole Glucan | 0.9981 | 4.1 | 0.088 | 0.60 |
| 374 After Extn. | 0.9995 | 4.1 | 0.103 | 0.44 |
| 377 Whole Glucan | 0.9997 | 4.1 | 0.091 | 0.45 |
| 377 After Extn. | 0.9995 | 4.1 | 0.103 | 0.44 |
| R4 Whole Glucan | 0.9995 | 2.5 | 0.087 | 0.66 |
| R4 After Extn. | 0.9988 | 2.5 | 0.103 | 0.44 |

$\phi_m$ = Maximum packing fraction

Table 10 summarizes the results of the carbohydrate assays from Examples 2, 3 and 4.

EXAMPLE 6

Treatment of whole glucan from Saccharomyces cerevisiae 264A with Laminarinase.

A 400 milliliter solution containing 1 milligram/milliliter whole glucan and 0.25 milligram/milliliter Laminarinase (endo $\beta$(1–3) glucanase) was prepared in phosphate buffer at pH 7.0. The solution is incubated at 37° C. for 4 hours. At the end of the incubation the solution is held at 70° C. for 15 minutes to deactivate the enzyme. The remaining residue is recovered by centrifugation at 500 rpm for 20 minutes. The resulting glucan residue is diluted into range of concentrations in order to obtain viscosity measurements of the Laminarinase degraded glucan sample. Since the enzyme cannot be effectively removed from solution, a control experiment was performed as above where the incubated enzyme contained no glucan. These readings were then used to correct the solvent viscosity accounting for the contribution of the enzyme to the macroscopic viscosity of the suspension. The effect of this process on the viscosity profile of an A364A glucan suspension is shown in FIG. 3.

TABLE 11

The Viscosity of Suspension of A364A Glucan Before and After the Enzyme Modification for a Range of Concentrations

| Source of Glucan | Viscosity in Centipoise, 25° C. | | | | |
|---|---|---|---|---|---|
| | 1% | 2% | 3% | 3.5% | 3.7% |
| A364A (Whole Glucan) | 1.4 | 2.7 | 13.7 | 127.3 | 816.3 |
| A364A (After Enzymatic Digestion) | 1.2 | 1.6 | 3.1 | 6.4 | 10.2 |

Table 11 shows the pronounced effect of the enzyme treatment on the glucan. At a concentration of 3.7% w/v an 80 fold decrease in the viscosity has been achieved.

EXAMPLE 7

Treatment of Whole Glucan From *Saccharomyces cerevisiae* 374 with Laminarinase.

A sample of 374 whole glucan was subjected to the process outlined in detail in Example 5. This process caused a decrease in the thickening properties of this glucan preparation as shown in Table 12 below:

TABLE 12

The Viscosity of a Suspension of 374 Glucan Before and After the Enzyme Modification for a Range of Concentrations

| | Viscosity in Centipoise, 25° C. | | | | |
|---|---|---|---|---|---|
| Source of Glucan | 1% | 2% | 3% | 3.5% | 3.7% |
| 374 (Whole Glucan) | 1.6 | 4.0 | 47.4 | 2630.7 | 146218.5 |
| 374 (After Enzymatic Digestion) | 1.3 | 2.3 | 9.3 | 62.9 | 302.3 |

EXAMPLE 8

Treatment of whole glucan from *Saccharomyces cerevisiae* 377 with Laminarinase.

A sample of 377 whole glucan was subjected to the process outlined in detail in Example 5. The effect of this process on this glucan preparation if similar to that on 374 glucan up to a concentration of 2% w/v. However, at higher concentrations the viscosity of the treated glucan is higher. This product therefore possesses extremely valuable properties since it has a negligible effect on suspension viscosities of low concentrations yet exhibits very high thickening properties at concentrations above 3% w/v. Table 13 below quantitatively describe the thickening properties of this product.

TABLE 13

The Viscosity of a Suspension of 377 Glucan Before and After the Enzyme Modification for a Range of Concentrations

| | Viscosity in Centipoise, 25° C. | | | | |
|---|---|---|---|---|---|
| Source of Glucan | 1% | 2% | 3% | 3.5% | 3.7% |
| 377 (Whole Glucan) | 1.6 | 3.4 | 16.0 | 75.0 | 193.5 |
| 377 (After Enzymatic Digestion) | 1.4 | 2.8 | 18.1 | 367.3 | 7477.4 |

The effect of this enzyme digest on the hydrodynamic properties of the glucan samples is summarized in Table 14.

TABLE 14

Hydrodynamic Properties of Glucan After Laminarinase Digest

| Sample | Regression Coefficient r | Shape Factor v | Hydrodynamic Volume v (dl/g) | $\emptyset_m$ |
|---|---|---|---|---|
| A364A Whole Glucan | 0.9999 | 2.5 | 0.106 | 0.46 |
| A364A After Digest | 0.9998 | 2.5 | 0.057 | 0.27 |
| 374 Whole Glucan | 0.9987 | 4.1 | 0.088 | 0.36 |
| 374 After Digest | 0.9985 | 4.1 | 0.070 | 0.30 |
| 377 Whole Glucan | 0.9974 | 4.1 | 0.091 | 0.45 |
| 377 After Digest | 0.9989 | 4.1 | 0.065 | 0.27 |

$\emptyset_m$ = Maximum packing fraction

We claim:

1. A process for preparing aqueous hydroxide insoluble whole glucan particles having substantially the three-dimensional structure of glucans, in vivo, comprising culturing a *Saccharomyces Cerevisiae* yeast strain in a culture medium, harvesting whole yeast cells from said culture medium, contacting said whole yeast cells with an aqueous hydroxide solution at a pH of from about 4.0 to about 12.5 or a normality of from about 0.75 to about 1.5 and a temperature of from about 25° C. to about 100° C. for a sufficient time to extract protein from said whole yeast cells to form aqueous insoluble whole glucan particles containing less than 1%, by weight, protein, said glucan particles substantially retaining the in vivo glucan three-dimensional structure and consisting essentially of glucans having $\beta(1-6)$ and $\beta(1-3)$ linkages.

2. Glucan particles produced by the method of claim 1.

3. A process of claim 1 wherein said *Saccharomyces Cerevisiae* whole yeast cells are harvested while they are in the log phase of growth.

4. Glucan particles produced by the method of claim 3.

5. A process of claim 3 wherein said *Saccharomyces Cerevisiae* yeast strain comprises *Saccharomyces Cerevisiae* A364A.

6. Glucan particles produced by the method of claim 5.

7. Glucan particles of claim 6 having a particle size of from about 2 to about 4 microns and sufficient to provide an aqueous suspension containing about 5.5 grams of said glucan particles per deciliter with a viscosity of about 1000 centipoise.

8. A process for claim 3 wherein said *Saccharomyces Cerevisiae* yeast strain comprises *Saccharomyces Cerevisiae* 374.

9. Glucan particles produced by the method of claim 8.

10. Glucan particles of claim 9 having a particle size of from about 2.5 to about 6.3 microns and sufficient to provide an aqueous suspension containing about 3.5 grams of said glucan per deciliter with a viscosity of about 2630 centipoise.

11. A method of claim 3 wherein said *Saccharomyces Cerevisiae* yeast strain comprises *Saccharomyces Cerevisiae* 377.

12. glucan particles produced by the method of claim 11.

13. Glucan particles of claim 12 having a particle size of from about 2.5 to about 5.0 microns and sufficient to provide an aqueous suspension containing about 3.5 grams of said glucan per deciliter with a viscosity of about 1636 centipoise.

* * * * *